(12) United States Patent
Wård

(10) Patent No.: US 6,651,652 B1
(45) Date of Patent: *Nov. 25, 2003

(54) METHOD FOR IDENTIFYING RESPIRATION ATTEMPTS BY ANALYZING NEUROELECTRICAL SIGNALS, AND RESPIRATION DETECTOR AND RESPIRATORY AID SYSTEM OPERATING ACCORDING TO THE METHOD

(75) Inventor: Leif Wård, Dalarö (SE)

(73) Assignee: Siemens-Elema AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/720,281
(22) PCT Filed: Jun. 10, 1999
(86) PCT No.: PCT/SE99/01022
§ 371 (c)(1), (2), (4) Date: Feb. 9, 2001
(87) PCT Pub. No.: WO00/00245
PCT Pub. Date: Jan. 6, 2000

(30) Foreign Application Priority Data

Jun. 30, 1998 (SE) .............................................. 9802335

(51) Int. Cl.⁷ ............................................. A61M 15/00
(52) U.S. Cl. ........................... 128/200.24; 128/202.13; 128/202.16; 607/42
(58) Field of Search ........................ 128/200.24, 202.13, 128/202.16; 607/2, 3, 20, 42

(56) References Cited

U.S. PATENT DOCUMENTS

| 4,237,899 A | * | 12/1980 | Hagfors et al. ............... 607/46 |
| 4,326,513 A | * | 4/1982 | Schulz et al. .......... 128/203.14 |
| 4,506,666 A | * | 3/1985 | Durkan .................. 128/204.23 |
| 4,681,121 A | * | 7/1987 | Kobal .................... 128/203.14 |
| 4,827,935 A | * | 5/1989 | Geddes et al. .............. 600/536 |
| 4,830,008 A | * | 5/1989 | Meer ......................... 600/534 |
| 4,928,674 A | * | 5/1990 | Halperin et al. ............ 600/495 |
| 5,036,848 A | * | 8/1991 | Hewson ...................... 600/380 |
| 5,056,519 A | * | 10/1991 | Vince .......................... 607/42 |
| 5,146,918 A | * | 9/1992 | Kallok et al. .................. 607/2 |
| 5,265,604 A | * | 11/1993 | Vince .......................... 607/42 |
| 5,584,290 A | * | 12/1996 | Brain .................... 128/204.22 |
| 5,678,535 A | * | 10/1997 | DiMarco ............... 128/200.24 |
| 5,953,713 A | * | 9/1999 | Behbehani et al. .... 128/204.18 |
| 6,149,670 A | * | 11/2000 | Worthen et al. ............ 607/104 |
| 6,198,970 B1 | * | 3/2001 | Freed et al. .................. 607/42 |
| 6,213,960 B1 | * | 4/2001 | Sherman et al. ............. 601/41 |
| 6,224,562 B1 | * | 5/2001 | Lurie et al. ................... 601/41 |
| 6,360,740 B1 | * | 3/2002 | Ward et al. ............ 128/200.24 |

\* cited by examiner

Primary Examiner—Weilun Lo
Assistant Examiner—Michael Mendoza
(74) Attorney, Agent, or Firm—Schiff Hardin & Waite

(57) ABSTRACT

A respiratory aid system has a device arranged for connection to a living creature in order to facilitate, support and/or control the respiration of the living creature. The device can be a ventilator or a neuroelectrical stimulation device. For faster and more efficient and more accurate respiratory aid the system contains a respiration detector, devised to pick up neuroelectrical signals from the living creature, identify respiration-related signals and send a control signal, related to the identified signals, to the device.

19 Claims, 3 Drawing Sheets

METHOD FOR IDENTIFYING RESPIRATION ATTEMPTS BY ANALYZING NEUROELECTRICAL SIGNALS, AND RESPIRATION DETECTOR AND RESPIRATORY AID SYSTEM OPERATING ACCORDING TO THE METHOD

BACKGROUND OF THE INVENTION

1. Field of the Invention

The present invention is directed to a method for identifying physiological attempts at respiration, as well as to a respiration detector and a respiratory aid system operating in accordance with the method.

2. Description of the Prior Art

Disease and injuries can make it necessary for a patient to receive respiratory aid. In principle, this respiratory aid can cover everything from facilitating a patient's spontaneous breathing to complete control of the patient's breathing. The type and degree of respiratory aid which is supplied depends, on the nature and scope of the disease/injury and the patient's treatment needs. Patients receiving anaesthesia (regardless of whether it is supplied because of disease/injury, for cosmetic surgery or for some other reason) may also need respiratory aid.

It should be noted that "patient" in this context relates to both people and animals.

Today, the most common way of providing respiratory aid is with ventilators (respirators) delivering a pressurised gas to the lungs. A number of ventilation modes are known, depending on which respiratory aid to supply. See for instance the article "Mechanical Ventilation", Chest 1993; 104; 1833–1859, which includes a discussion relating to objectives and recommendations regarding mechanical ventilation.

Another way to provide respiratory aid is to apply extracorporeal pressure around the entire thorax and midriff (e.g. the classic 'iron lung' used for e.g. patients whose respiratory muscles have been damaged by polio). A device of this kind is disclosed in U.S. Pat. No. 5,222,478.

Another way to induce breathing is by means of electrical stimulation. Either by direct stimulation of the muscles of the diaphragm in particular or by indirect stimulation via the nervous system, in particular the phrenic nerve. A diaphragmatic pacer is disclosed in U.S. Pat. No. 5,056,519. A nerve stimulator for treatment of respiratory disorders is disclosed in PCT publication WO 93/01862.

Stimulation of the respiratory system can also be made magnetically, as disclosed in U.S. Pat. No. 5,857,957.

One problem shared by all respiratory aid is to obtain information on when the patient needs to breathe and how much the patient needs to breathe. This is particularly the case for completely controlled respiratory aid with mechanical ventilation.

In completely controlled respiratory aid the physician bears the main responsibility for programming appropriate respiration parameters, such as respiratory rate, tidal volume, inspiration duration etc.

Measurement of physical parameters related to metabolism, such as oxygenation of blood, the carbon dioxide content of blood etc can be of help for the physician when programming the respiration parameters. Some of the physical parameters can be estimated from accurate analysis of the contents of expired gas. The measurements of physiological are too imprecise to provide enough information for individual breath to breath control but can supply important information for the overall regulation of respiratory rate etc.

For patients that can breath spontaneously, at least in part, information of the patients breathing can be determined. When pressure, flow and/or changes in temperature inside or outside the patient's airways are sensed, the patient's spontaneous attempts to breathe can be detected and used for triggering the respiratory aid. The magnitude of each attempt to breathe can also be determined and used to affect the magnitude or type of respiratory aid. This option is mainly useful in supported respiration aid.

One problem in supported respiration aid is that the patient's spontaneous attempts of breathing come in conflict with the supportive respiration aid. This is normally referred to as competition. One way of avoiding competition is to sedate the patient and use completely controlled respiratory aid only.

The above mentioned physical parameters can of course also be used for spontaneously breathing patients for determining when a patient needs to breathe.

Lung movements can also be measured by measuring the impedance across the chest (and lungs). Lung movements are also indicative of attempts to breathe.

Direct measurement of the musculature participating in respiration can also provide information relating to attempts to breathe.

Common to all these procedures is the circumstance that none of them provide an accurate physiological picture of the patient's true respiratory needs.

Breathing is part of the body's autonomic system. One important known factor affecting this autonomic system is the body's own chemical receptors that sense carbon dioxide content. But the autonomic system is also affected by a number of other physiological factors. Some of these factors are probably still unknown to the medical expertise.

SUMMARY OF THE INVENTION

An object of the invention is to provide a respiratory aid system designed for determining, more reliably and efficiently than in known systems, when a patient wishes to or needs to breathe.

Another object of the invention is to provide a respiration detector capable of more rapid and efficient sensing of a patient's attempts at breathing than in known detectors.

Another object of the invention is to provide a method for identifying physiological attempts to breathe.

A patient's true respiratory need can be established by registering neuroelectrical signals and extracting the signal components related to respiration. In other words, the nerve impulses are detected and used to extract information. The nerve impulses contain information about a patient's respiratory needs that automatically comprises all physiological functions with an impact on respiration. True respiratory needs can be utilised for controlling a device supplying respiratory aid. In particular, the point in time for each individual breath (initiated by the patient) can then be determined from the neurological signals, but these signals also contain about all the information essential to individual breaths.

In principle, all kinds of known apparatuses for respiratory aid, such as ventilators, anaesthetic machines, nerve stimulators, muscle stimulators and magnetic stimulators, can be used, where or when appropriate with regard to the conditions in each specific case.

Neuroelectrical signals (nerve impulses) related to respiration originate in the respiratory centre of the medulla oblongata, and these signals can, in principle, be collected from the respiratory centre or picked up along the nerves carrying the signals to the respiratory musculature. The phrenic nerve has proved to be particularly suitable for use as a result of its location. Signals can be picked up with an extracorporeal sensor arrangement placed on the skin, with a needle-shaped sensor means adapted to puncture the skin to get close to (or in contact with) the nerve or with a sensor designed to be placed on a surgically exposed nerve. An implanted sensor arrangement could also be considered, in particular for long-term treatment.

One version of the respiratory aid system utilizes sensor signals related to breathing for triggering an inspiration by the patient. The triggering can be adapted so inspiration occurs at a phase in which the patient would have breathed spontaneously. In completely controlled respiratory aid, this would provide a patient-related respiratory rate. In supported respiration, this would also lead to a much faster response to the delivery of respiratory assistance than in prior art technology. Competition between the patient and the ventilator can be avoided.

In cases in which the patient has a varying capacity or ability to breathe spontaneously, a respiratory sensor can be used for determining whether a respiratory signal from the respiratory centre really leads to a spontaneous inspiration or an attempt at inspiration. This kind of respiratory sensor can also be used for determining the strength of an inspiration/attempt at inspiration.

If a spontaneous inspiration does occur, triggering is not always necessary and can be completely inhibited in some instances. The respiratory aid system could instead be devised to provide supplementary support (possibly according to information derived from the neurological signals) for a spontaneous inspiration when the latter is inadequate. For example, the patient's respiratory musculature might be too weak to sustain physiological inspiration duration.

With a respiration detector for sensing the respiration-related part of the patient's nervous system, attempts at respiration can be detected at the earliest possible stage and used for controlling a device for supplying respiratory aid.

DESCRIPTION OF THE PREFERRED EMBODIMENTS

Figure 1:
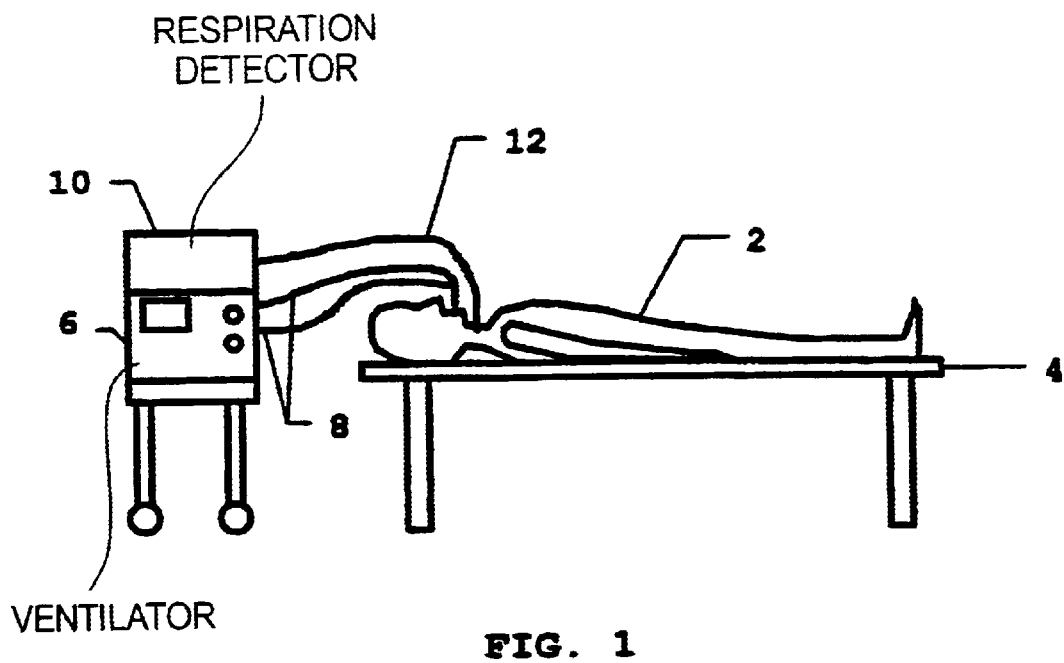
FIG. 1 shows a first embodiment of a respiratory aid system constructed and operating in accordance with the principles of the present invention.

FIG. 1 shows a patient 2 on a bed 4. The patient 2 is connected to a ventilator 6 by a tubing system 8 in order to receive respiratory aid from the ventilator 6. In principle, the ventilator 6 can be a known ventilator, such as the Servo Ventilator 300, Siemens-Elema AB, Sweden, or some other known respirator (including home-care breathing aid, CPAP-machines, resuscitation machines etc.) or anaesthetic machine. In principle, respiratory aid can consist of any conventional respiratory assistance given to patients who have or stand a risk of getting difficulty in achieving or are unable to achieve adequate spontaneous respiration.

A respiration detector 10 is connected to the ventilator 6 and, via a signal line 12, to the patient's 2 phrenic nerve. Here, the signal line 12 can be transcutaneously connected to the phrenic nerve or indirectly connected to the phrenic nerve from the surface of the skin. Neuroelectrical control signals for respiration, generated in the respiratory centre of the medulla oblongata, are carried along the phrenic nerve to the diaphragm (in particular). These signals are picked up by the signal line 12 and sent to the respiration detector 10.

The respiration detector 10 extracts the relevant signals related to respiration. Identification can be made using known signal processing methods. Signals concerning respiration or, the function of the diaphragm in this case, usually arrive as a train of impulses. The respiration detector 10 then generates a control signal, sent to the ventilator 6, according to respiration signals detected. More advanced analysis of the nerve impulses can be made with more advanced methods, inter alia including pattern recognition systems and artificial neural networks (ANN).

These respiratory signals are the earliest indication that the patient 2 wants to breathe. These signals can also supply information on the physiological need of the patient 2 to breathe. The latter is in particular valid for patients 2 whose inability to breathe sufficiently is unrelated to injuries to or some impact on the respiratory centre.

One advantage of obtaining the respiratory signal at an early stage is that the respiratory aid (provided by a ventilator 6 in this instance) can be supplied according to the 2 true physiological needs and not according to estimated needs or needs calculated in some other way. Moreover, respiration will have the most natural rhythm for the patient 2. Thus the triggering of inspiration phases is an essential part of the invention, but the neurological signals contain more intelligence than just information on when the patient should take a breath. In principle, they contain all the information essential to each individual breath, especially respiratory depth, inspiration duration and any inspiration pause. Some physiological respiratory control also concerns expirations, even if expiration is a normally passive process occurring when the respiratory musculature relaxes.

Since an inspiration phase can be started in synchrony with the actual inspiration of the patient 2, breathing effort can be greatly reduced for patients 2 retaining some ability to breathe spontaneously.

Figure 2:
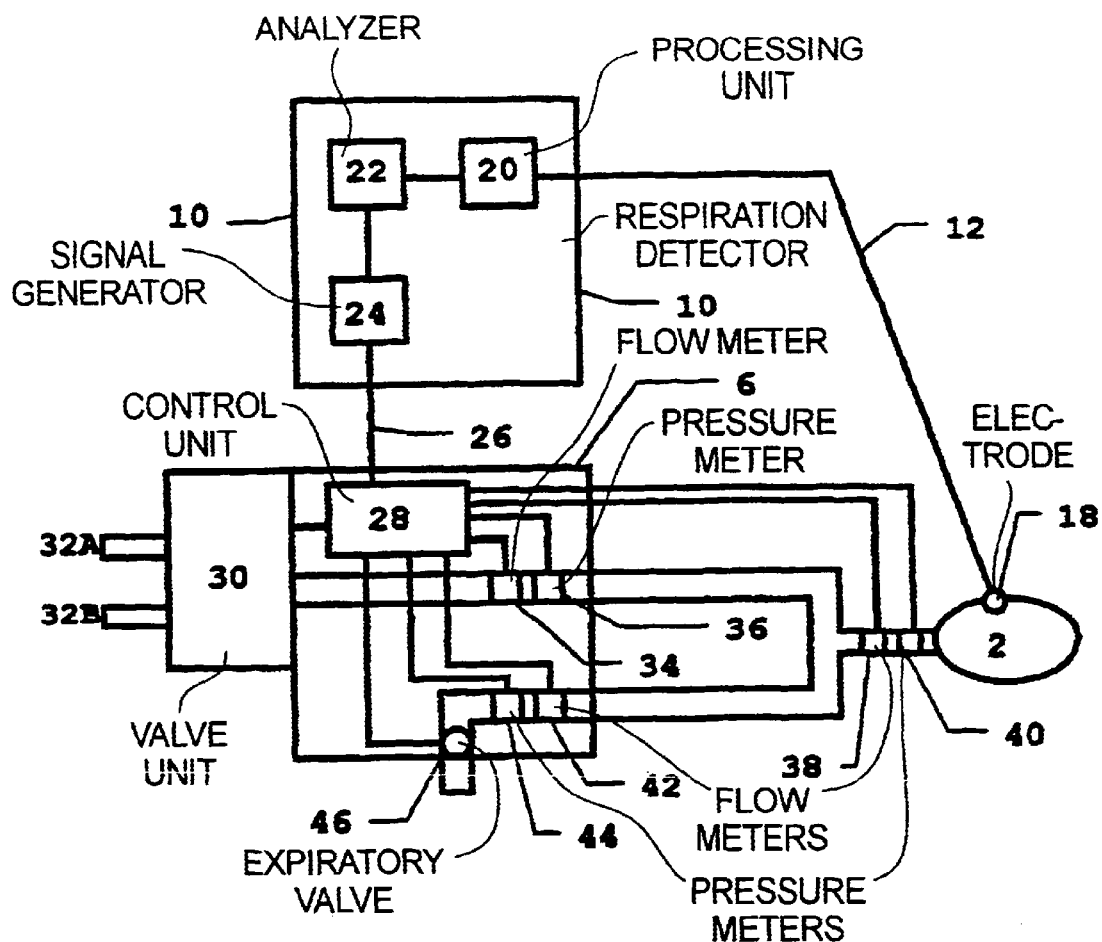
FIG. 2 shows one embodiment of a respiration detector and a ventilator according to the invention.

A respiratory sensor can be used in parallel with patients 2 with a greater ability to breathe spontaneously so the control signal from the respiration detector 10 can be inhibited. This is illustrated in FIG. 2 in which the ventilator 6 and respiration detector 10 are depicted in greater detail.

The respiration detector 10 is connected to the patient 2 by an electrode 18 for sensing the neuroelectrical signals. Sensed signals are sent to a signal processing unit 20 for filtration and amplification in some suitable fashion. The processed signals are then sent to an analyzer 22 for signal identification. Appropriate signal analysis can establish when the patient 2 wishes to breathe spontaneously and the extent to which the patient 2 wishes to breathe. Respiratory signals mainly consist of a train of impulses to the respiratory musculature (especially to the diaphragm in this example, since the phrenic nerve is being sensed).

Information on the presence of respiratory signals is sent to a signal generator 24 that generates a control signal depending on the respiratory signals identified. This control signal is sent via a control line 26 to a control unit 28 in the ventilator 6.

The control unit 28 regulates the ventilator 6 according to parameters set by a physician and parameters measured by the ventilator 6.

A breathing gas is mixed to the right composition, pressure and flow in a valve unit 30. Different gases can be connected in the known fashion via a first gas connector 32A and a second gas connector 32B.

Measurement of pressure and flow can be performed in different parts of the system by a first flow meter 34, a first pressure meter 36, a second flow meter 38, a second pressure meter 40, a third flow meter 42 and a third pressure meter 44. When pressure and/or flow is/are measured, an initiated breath can be sensed as a change in pressure and /or flow. The control unit 28 plus one or more of aforementioned meters thereby constitutes a respiration sensor. These meters are therefore only shown to illustrate that measurement of pressure and flow can be made at one or a number of locations in the system.

If the patient 2 commences a breath by drawing in air, the control signal's effect on the control device 28 is reduced, delayed or inhibited. A sufficiently strong spontaneous breath within a specific period of time after the respiration detector 10 senses a respiratory signal means that the patient 2 does not need respiratory aid during that breath, other than a supply of breathing gas. In these circumstances, the ventilator 6 can operate as a normal ventilator 6 and support the patient 2 according to a pre-determined pattern or according to the strength of the spontaneous breathing by the patient 2.

In principle, the respiration detector 10 can also sense when the patient 2 wishes to exhale and then send a signal to the ventilator 6 to permit the start of an exhalation (expiration). This spares the patient 2 the inconvenience of actively building up enough pressure in the lungs to activate the expiratory phase. During expiration, an expiratory valve 46 can be regulated to maintain an appropriate positive end expiratory pressure (PEEP) for the patient 2.

Figure 3:
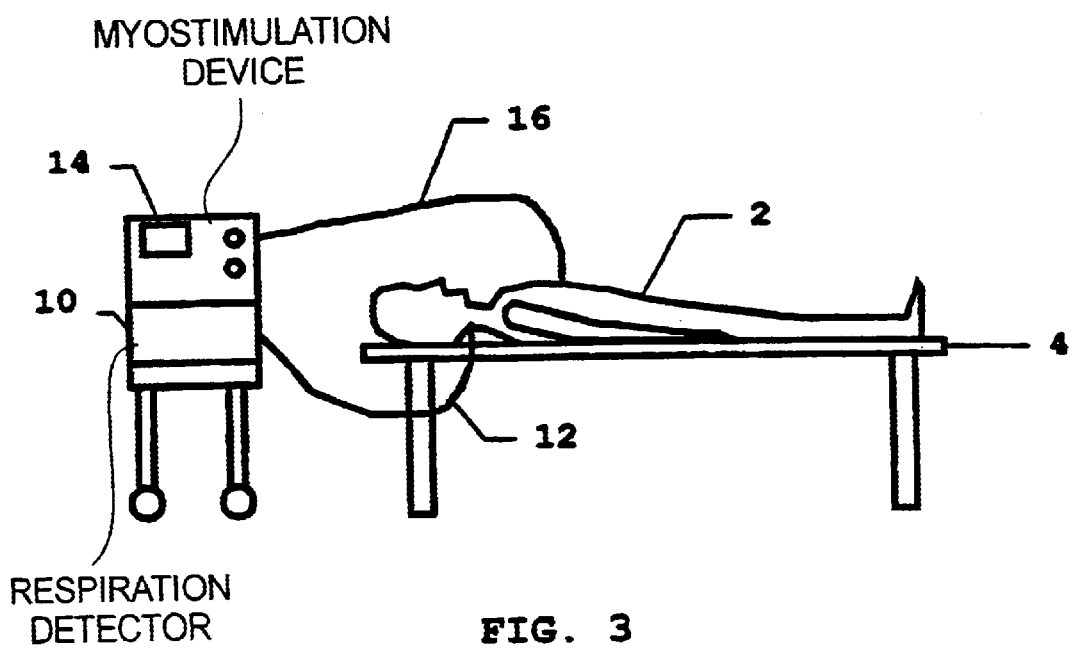
FIG. 3 shows a second embodiment of a respiration detector and a ventilator according to the invention.

FIG. 3 shows an alternative design for the respiratory aid system according to the invention. A patient 2 placed on a bed 4 is connected to a respiration detector 10 by an electrode line 12. In this instance, the electrode line 12 is devised to sense signals in the respiratory centre itself or in nerve pathways that mainly carry respiratory signals to the respiratory musculature around the thorax.

A myostimulation device 14 is connected to the musculature at the diaphragm of the patient 2 via stimulation line 16 in order to stimulate the diaphragm's muscles with electrical signals and accordingly induce an inspiration.

Figure 4:
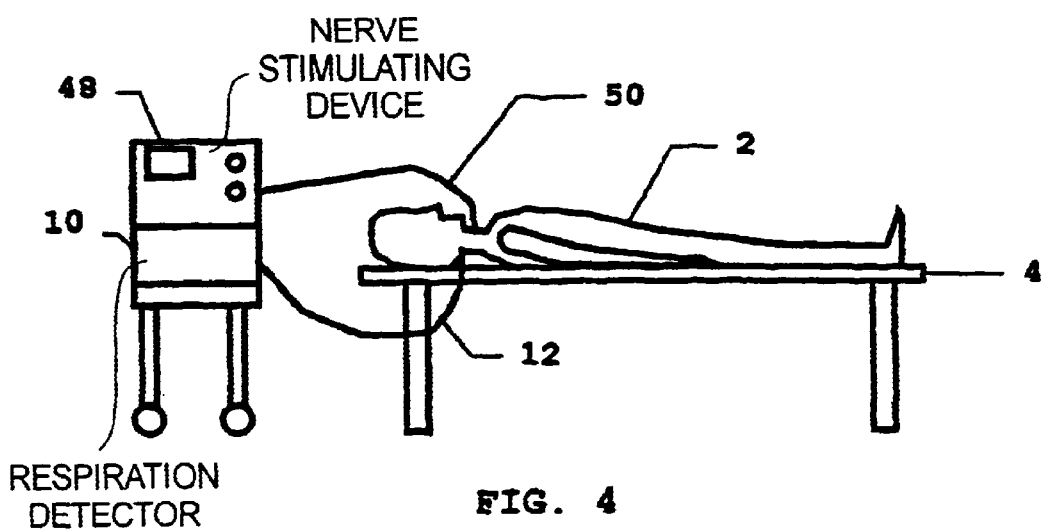
FIG. 4 shows a third embodiment of a respiration detector and a ventilator according to the invention.

Alternately, as shown in FIG. 4, a nerve stimulating device 48 can be used for stimulating the respiratory nerves via a stimulation line 50. In this instance the phrenic nerve is stimulated. This can be used in cases where there is a fault in the nervous system which prevents a natural passage of impulses from the respiratory centre to the muscle. A nerve stimulation "downstream" the fault can then maintain as normal respiration as possible. In the alternative, the impulses can be enhanced by superimposing the stimulation signal from the nerve stimulating device 48.

Figure 5:
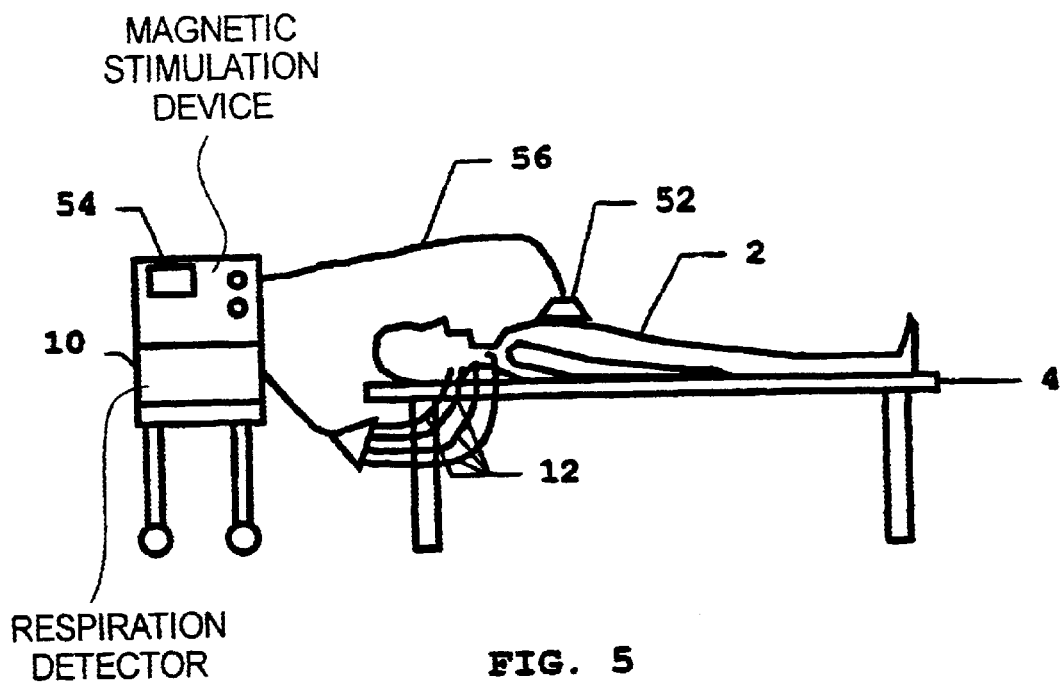
FIG. 5 shows a fourth embodiment of a respiration detector and a ventilator according to the invention.

FIG. 5 shows another alternative, where a magnetic stimulation device 52 is arranged over the lung region of the patient 2 for magnetic stimulation of the respiratory system. The magnetic stimulation device 52 is controlled and powered by a control unit 54 via a line (or set of lines) 56. In the specific embodiment of FIG. 5, the nerve impulses of the patient 2 are detected at several places via a multitude of electrodes 12.

Figure 6:
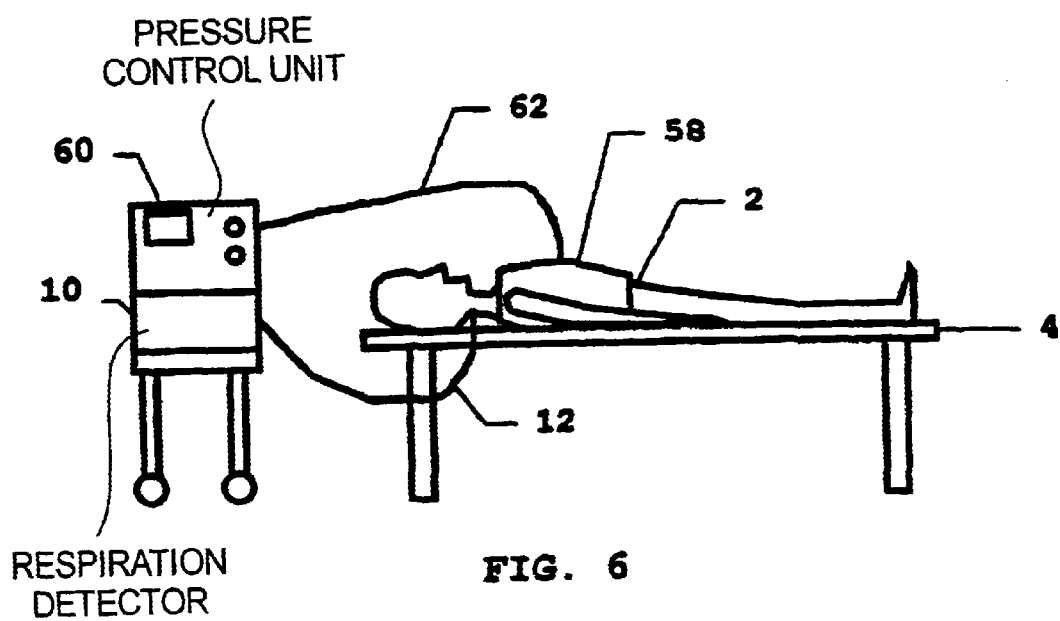
FIG. 6 shows a fifth embodiment of a respiration detector and a ventilator according to the invention.

Finally, FIG. 6 shows another alternative, where a casing 58 placed around the upper part of the patient 2 provides the respiratory aid. Pressure generated by the casing 58 is controlled and supplied by control unit 60 via pressure line 62.

The respiratory aid devices and nerve impulse detection devices shown in the embodiments can be combined where suitable. For instance, a multitude of sensing electrodes (FIG. 5) can be used to sense the nerve impulses in the embodiment showing a ventilator (FIG. 1).

Although modifications and changes may be suggested by those skilled in the art, it is the intention of the inventor to embody within the patent warranted hereon all changes and modifications as reasonably and properly come within the scope of his contribution to the art.

I claim:

1. A respiratory aid system comprising:
    a device adapted for connection to a living subject for assisting breathing by said subject;
    a sensor adapted for interaction with said subject for picking up neuroelectrical signals from said subject;
    an analyzer supplied with said neuroelectrical signals for identifying signals relating to respiration by said subject from said neuroelectrical signals; and
    a control signal generator, connected to said analyzer and to said device, for generating a control signal from said signals relating to respiration and for supplying said control signal to said device to control said device to assist said breathing.

2. A respiratory aid system as claimed in claim 1 wherein said sensor is adapted to pick up neuroelectrical signals from a respiratory center of said subject.

3. A respiratory aid system as claimed in claim 1 wherein said sensor is adapted to pick up neuroelectrical signals from any nerve in said subject connecting a respiratory center of said subject with respiratory musculature of said subject.

4. A respiratory aid system as claimed in claim 1 wherein said sensor is adapted to pick up neuroelectrical signals from the phrenic nerve of said subject.

5. A respiratory aid system as claimed in claim 1 wherein said device is a ventilator, and wherein said ventilator triggers an inspiration phase by generating a flow of breathing gas in response to said control signal.

6. A respiratory aid system as claimed in claim 1 wherein said device is a myostimulator, and wherein said myostimulator triggers an inspiration phase by generating and emitting a myostimulation signal in response to said control signal.

7. A respiratory aid system as claimed in claim 1 wherein said device is a nerve stimulator, and wherein said nerve stimulator triggers an inspiration phase by generating and emitting a nerve stimulation signal in response to said control signal.

8. A respiratory aid system as claimed in claim 1 wherein said device is a magnetic stimulator, and wherein said magnetic stimulator triggers an inspiration phase by generating and emitting a magnetic stimulation signal in response to said control signal.

9. A respiratory aid system as claimed in claim 1 wherein said device is a chamber respirator having an enclosure adapted to enclose at least a part of the body of the subject, and wherein said chamber respirator triggers an inspiration phase by generating a pressure variation in said enclosure in response to said control signal.

10. A respiratory aid system as claimed in claim 1 further comprising a respiration sensor, operating independently of said sensor for picking up neuroelectrical signals, adapted for interaction with said subject to detect spontaneous respiration, said respiration sensor being connected to said control unit and generating a detection signal when spontaneous breathing is sensed by said respiration sensor which overrides said control signal.

11. A respiratory aid system as claimed in claim 10 wherein said respiration sensor identifies a magnitude of said spontaneous breathing and wherein said detection signal contains information identifying said magnitude of spontaneous breathing, and wherein said device triggers an inspiration phase dependent on said magnitude of spontaneous breathing identified in said detection signal.

12. A respiratory aid system comprising:
   a first device adapted for interacting with a respiration-related portion of a nervous system of a respiration subject for generating a control signal when a physiological attempt at breathing is sensed from said subject; and
   a second device, supplied with said control signal, adapted for interaction with said subject for providing respiratory aid to said subject dependent on said control signal.

13. A respiratory aid system as claimed in claim 12 wherein said second device is a ventilator, and wherein said ventilator triggers an inspiration phase by generating a flow of breathing gas in response to said control signal.

14. A respiratory aid system as claimed in claim 12 wherein said second device is a myostimulator, and wherein said myostimulator triggers an inspiration phase by generating and emitting a myostimulation signal in response to said control signal.

15. A respiratory aid system as claimed in claim 12 wherein said second device is a nerve stimulator, and wherein said nerve stimulator triggers an inspiration phase by generating and emitting a nerve stimulation signal in response to said control signal.

16. A respiratory aid system as claimed in claim 12 wherein said second device is a magnetic stimulator, and wherein said magnetic stimulator triggers an inspiration phase by generating and emitting a magnetic stimulation signal in response to said control signal.

17. A respiratory aid system as claimed in claim 12 wherein said second device is a chamber respirator having an enclosure adapted to enclose at least a part of the body of the subject, and wherein said chamber respirator triggers an inspiration phase by generating a pressure variation in said enclosure in response to said control signal.

18. A respiratory aid system as claimed in claim 12 further comprising a response sensor adapted for interaction with said subject to sense a response of said subject to said physiological attempt at respiration and for generating a detection signal and for supplying said detection signal to said second device, said second device adapting said respiratory aid dependent on said detection signal.

19. A method for identifying a physiological attempt at respiration by a respirating subject, comprising the steps of:
   picking up neuroelectrical signals originating in a respiratory center of a respirating subject;
   filtering components out of said neuroelectrical signals related to respiration;
   identifying respiratory signals related to attempts at respiration from said signal components; and
   generating a triggering signal for triggering an inspiration phase dependent on said respiratory signals.

* * * * *